US011951468B2

(12) United States Patent
Schafrinski (10) Patent No.: US 11,951,468 B2
(45) Date of Patent: Apr. 9, 2024

(54) LABORATORY CABINET DEVICE FOR STORING LABORATORY SAMPLES, COMPRISING A MAGNETIC CLOSURE

(71) Applicant: Eppendorf SE, Hamburg (DE)

(72) Inventor: Arne Schafrinski, Hamburg (DE)

(73) Assignee: EPPENDORF SE, Hamburg (DE)

( * ) Notice: Subject to any disclaimer, the term of this patent is extended or adjusted under 35 U.S.C. 154(b) by 773 days.

(21) Appl. No.: 16/981,265

(22) PCT Filed: Mar. 14, 2019

(86) PCT No.: PCT/EP2019/056437
§ 371 (c)(1),
(2) Date: Sep. 15, 2020

(87) PCT Pub. No.: WO2019/175320
PCT Pub. Date: Sep. 19, 2019

(65) Prior Publication Data
US 2021/0039082 A1    Feb. 11, 2021

(30) Foreign Application Priority Data
Mar. 16, 2018  (EP) .................................... 18162381

(51) Int. Cl.
*B01L 1/02* (2006.01)
*C12M 1/00* (2006.01)
*E05B 1/00* (2006.01)

(52) U.S. Cl.
CPC .............. *B01L 1/025* (2013.01); *C12M 41/14* (2013.01); *E05B 1/003* (2013.01); *E05Y 2201/22* (2013.01); *E05Y 2201/462* (2013.01); *E05Y 2900/20* (2013.01)

(58) Field of Classification Search
CPC .... B01L 1/025; C12M 41/14; E05Y 2900/20; E05Y 2201/22; E05Y 2201/462; E05B 1/003
See application file for complete search history.

(56) References Cited

U.S. PATENT DOCUMENTS

| 2,340,864 | A | * | 2/1944 | Carpenter | ............. E04B 1/6183 |
| | | | | | 292/108 |
| 5,810,709 | A | | 9/1998 | Simenauer et al. | |
| 5,813,711 | A | | 9/1998 | Sauvagnat | |
| 6,076,891 | A | * | 6/2000 | Bernhardt | ............. A47C 7/541 |
| | | | | | 297/411.31 |
| 6,120,119 | A | | 9/2000 | Jelinski et al. | |
| 2006/0049645 | A1 | | 3/2006 | Drumm | |
| 2006/0137409 | A1 | | 6/2006 | Fawcett et al. | |
| 2006/0170225 | A1 | | 8/2006 | Macken | |
| 2009/0125024 | A1 | | 5/2009 | Baur | |

(Continued)

FOREIGN PATENT DOCUMENTS

| CN | 1206490 A | 1/1999 |
| CN | 103758442 A | 4/2014 |

(Continued)

*Primary Examiner* — Matthew W Ing
(74) *Attorney, Agent, or Firm* — Todd Lorenz (57) ABSTRACT

The invention relates to a laboratory cabinet device for storing laboratory samples with a magnetic closure for the door. It in particular relates to a tempering cabinet for tempering laboratory samples, in particular, an incubator for the growth of cell cultures.

11 Claims, 5 Drawing Sheets

(56) References Cited

U.S. PATENT DOCUMENTS

| | | | |
|---|---|---|---|
| 2011/0296653 A1* | 12/2011 | Fiedler | E05C 19/06 |
| | | | 403/321 |
| 2012/0043768 A1 | 2/2012 | Graham | |
| 2015/0351537 A1* | 12/2015 | Grabowski | A47B 13/021 |
| | | | 24/303 |

FOREIGN PATENT DOCUMENTS

| | | | | |
|---|---|---|---|---|
| CN | 204663163 U | | 9/2015 | |
| CN | 206228010 U | | 6/2017 | |
| CN | 206429094 | | 8/2017 | |
| DE | 97706 A1 | | 5/1973 | |
| DE | 3610654 | | 10/1986 | |
| DE | 8902181 U1 | | 5/1989 | |
| EP | 0238313 A1 | | 9/1987 | |
| EP | 1568836 A2 | | 8/2005 | |
| GB | 2193725 A | * | 2/1988 | B01L 7/00 |
| JP | 2017076799 A | | 4/2017 | |

\* cited by examiner

LABORATORY CABINET DEVICE FOR STORING LABORATORY SAMPLES, COMPRISING A MAGNETIC CLOSURE

The present disclosure relates to a laboratory cabinet device for storing laboratory samples with a magnetic closure for the door. It in particular relates to a tempering cabinet for tempering laboratory samples, in particular, an incubator for the growth of cell cultures.

Such incubators are used in biological and medical laboratories to keep cells in cell culture under controlled environmental conditions, thus enabling the growth of living cells in vitro. For this purpose, the temperature and the gas composition or the humidity of the atmosphere inside an incubator chamber isolated from the environment are kept at the desired values by the apparatus devices of the incubator. Eukaryotic cells require $CO_2$ incubators. The atmosphere is formed by air with a certain $CO_2$ and $O_2$ content and a certain humidity, a suitable temperature is often 37° C. Such temperature control cabinets have a chamber for storing laboratory samples, with a chamber opening through which the user stores and retrieves the samples inside the chamber.

The chamber door should reliably close the chamber interior. For this purpose, various technical solutions are known in the prior art. Mechanically acting closures have, for example, a bolt closure, a tension closure or a latch closure, which must be unlocked to open. Such mechanical solutions are complex and generate mechanical vibrations on the housing. Single-handed actuation is often difficult to achieve with known latch closures, but would be desirable. In practice, the user holds in one hand a sample vessel that he has taken from the inside of the chamber or that he wants to insert into the inside of the chamber. Thus, the user typically has only one hand free to actuate a closure mechanism of the chamber door. Since spillage or excessive movement of the mostly liquid laboratory sample in the sample container must be avoided, the actuation of the closure should be intuitive and safe and the user should be able to focus his attention on the safe handling of the sample.

In order to protect the stored laboratory samples, it is particularly important in the case of laboratory cabinet devices or temperature control cabinets to minimize the time during which the interior of the cabinet is exposed to the environment. The present invention is based on the observation that the opening time intervals can be influenced by the design of the closing mechanism with which the chamber door is held and closed in the closed position. Therefore, a laboratory cabinet device with a closure device was developed, which can be actuated efficiently by the user to minimize the opening time.

It is therefore an object of the present invention to specifying a laboratory cabinet device whose chamber door closure can be actuated efficiently.

The invention solves this problem by the laboratory cabinet device according to claim 1.

Preferred embodiments are in particular subject of the dependent claims.

The configuration of the closure device of the laboratory cabinet device, in particular the configuration of the actuating element with a grip tab portion and the possibility of overcoming the magnetic holding force both by swiveling the actuating element and by pulling on the actuating element, results in an efficiently operable laboratory cabinet device. Since the user always has the choice of opening the closure device either by swiveling or by pulling, an incubator equipped with the inventive closure device can always be actuated efficiently by both right-handed and left-handed users. The use of the magnetically interacting holding elements eliminates the requirement of conventional bolt closures acting by means of mechanical form closure to first swivel the actuating element before opening the chamber door or to hold the actuating element in a swiveled position before closing the chamber door. The grip tab portion allows intuitive actuation of the operating element. Almost every movement of the grip tab portion intuitively performed by the user results in the desired opening or closing of the magnetic closure.

Therefore, during the operating time of the incubator, the time needed for different users to learn and complete the operation of the chamber door closure is reduced. In particular, one-handed actuation of the closure device is facilitated, since the actuation is independent of the subjective preferences of the user, actuation with the right or left hand or even with another part of the body or aid, and regardless of whether the closure device is mounted on the left or right side of the chamber door. The time during which the interior of the chamber is exposed to the environment is minimized by the closure device. The closure device can be optimally integrated into the laboratory cabinet device, as the space required for the closure device on the laboratory cabinet device is small due to the compact space requirements of the grip tab portion.

The laboratory cabinet device for storing laboratory samples is, in particular, a tempering cabinet for tempering laboratory samples. Such devices are electrically operated and have a voltage connection. The holding device preferably works with one or more permanent magnets, so that the holding device is independent of the power supply. The closure of the housing door is therefore guaranteed even if the power supply fails. Instead of the magnetically interacting holding elements, a connecting device can also be used, which provides a clamp connection, in particular a snap-in connection. In particular, such a clamp connection can be configured such that it can be overcome both by swiveling the actuating element and by pulling on the actuating element. The subject matter of the invention therefore also relates to a laboratory cabinet device, whereas the closure device of which comprises, alternatively and/or additionally to the magnetically interacting holding elements (first and second holding element), at least two holding elements which can be connected via a clamp connection.

The temperature control cabinet regulates the temperature of the laboratory samples, i.e. it keeps the inside of the chamber and thus the laboratory samples stored there within the scope of tolerances by temperature control at a setpoint temperature that can, in particular, be set by the user.

This can be above room temperature (ambient temperature), as is the case with a warming cabinet or incubator, or below room temperature, as is the case with a refrigerator or freezer. In the case of a laboratory cabinet configured as a climate chamber, preferably also a climate parameter, which characterizes the inside of the chamber, is controlled within tolerances. This climate parameter can be the air humidity, and/or a gas concentration, e.g. a $CO_2$, $N_2$ and/or $O_2$ concentration. Such a climate chamber is, for example, an incubator for laboratory samples consisting of living cell cultures.

The actuating element is preferably a plate-shaped, a preferably essentially flat, component. In particular, the actuating element is not larger than a cuboid with dimensions (length×width×height) of preferably 20 cm×10 cm×4 cm, preferably 15 cm×6 cm×3 cm. The actuating element preferably has at least one recess and/or cavity. Such a recess or cavity can be used advantageously to accommodate further functional components and reduce weight and manufacturing costs. The actuating element preferably comprises an elongated basic body, in particular a plate body, which comprises the grip tab portion as a first end and a second end. A hole or recess is preferably provided between the ends of the basic body, through which a rotation axis can be guided perpendicular to the swivel plane and to the plate plane of the basic body respectively. A rotary axis element can be a metal pin element that is attached to the chamber door. By means of the rotary axis element, the actuating element is preferably mounted pivotably on the chamber door.

The actuating element fixed to the chamber door has a pivoting plane to which the actuating element always runs parallel when it is pivoted between the first and second pivoting position. The actuating element has a lower side facing the chamber door and an upper side facing away from the chamber door and in particular facing towards the user.

The grip tab portion is preferably formed integrally with the actuating element, so that the actuating element can be loaded mechanically and can be used reliably over the entire service life of the laboratory cabinet device. The grip tab portion can also be a separate part that is connected to the actuator. The grip tab portion can, in particular, comprise a deformable or soft portion. The portion can in particular consist of an elastomer, e.g. silicone, and can be configured as a cover or casing for the grip tab portion or the entire actuating element. The gripping of the grip tab portion can be facilitated or made more comfortable by an elastomer.

The grip tab portion preferably comprises an edge formed at the first end of the actuating element, which comprises a bend running around the axis of rotation. Through this configuration, a user associates handling with a swivel movement, so that the actuating element can be actuated intuitively. In particular, the bend edge can follow a circumference of a circle, which in particular can be concentric to the axis of rotation.

The grip tab portion preferably comprises the first holding element on its lower side facing the front of the chamber housing in the closed position. The first holding element can also lead to the upper side of the actuating element or protrude from the upper side. The first holding element can also form the first end of the actuating element.

The grip tab portion preferably comprises at least one tab portion which, in the second pivot position in the pivot plane of the actuating element, projects beyond the edge of the chamber door and also projects beyond the extent of the first holding element in this pivot plane. By extending the tab portion into the swivel plane, a space-saving handle can be realized, which allows reliable and comfortable actuation of the actuating element and the entire chamber door.

The grip tab portion can, in particular, comprise at least one, in particular two, wing portions each configured as tab portions, which are in particular formed integrally with the grip tab portion or the actuating element. The wing portions protrude laterally from the plate body of the actuating element and parallel to the pivoting plane of the plate body or to the main plane of the chamber door, so that in the pivoting position P2 a finger of the user can engage behind the first and/or second wing portion to open the chamber door by pulling. The grip tab portion and the wing portions protrude laterally, especially with respect to the first holding element and parallel to the pivoting plane of the panel body or to the main plane of the chamber door, so that it is easier to reach behind the grip tab portion. This special design is ergonomically advantageous, in particular, it creates an easily accessible space for the intervening fingers.

The first holding element can be a plate element, which is inserted into a recess on the lower side of the grip tab portion and which is screwed and/or glued in place. The holding element can also be spring-mounted on the actuating element in order to allow an evasive movement of the holding element in a direction perpendicular to the pivoting plane of the plate body or respectively to the main plane of the chamber door.

In the closed position of the chamber door and in the swivel position P2 of the actuating element, the first and second holding elements adjoin against each other and adhere to each other due to the magnetic attraction force—and/or due to a clamping force. By turning the actuating element from position P2 to position P1, this attraction force can be overcome more easily and comfortably than by pulling in direction A. In the open position of the chamber door, when the actuating element is arranged in position P2, in particular the closing of the chamber door automatically leads to the closing of the magnetic closure, in that in the area of influence of the magnetic force the magnetic holding force moves the first and second holding elements directly towards each other. The closure device is preferably configured in such a way that the striking of the holding elements—in particular as a "click"—can be perceived acoustically, so that the user receives an acoustic feedback about the successful closing of the chamber door.

The closure device preferably comprises a position latching device by means of which the actuating element engages at least in the second swivel position and/or at least also engages in a first swivel position. In the second swivel position, the actuating element is preferably arranged horizontally, i.e. its longitudinal axis L extends horizontally. In the first swivel position, the actuating element is preferably arranged vertically, i.e. its longitudinal axis L extends vertically.

The position latching device comprises at least one latching element, preferably several latching elements, preferably exactly one latching element, preferably exactly two latching elements and especially preferably exactly three latching elements. The latching element(s) can be arranged on a carrier element, which can in particular be configured as a latching element plate on which at least one latching element is arranged. The at least one latching element interacts with at least one latching portion to realize a latching position or a latched swivel position. The latching portion can be part of a height profile, which can be formed in a height profile portion. The at least one latching element, in particular the carrier element, can be fixed to the chamber door and the at least one latching portion, in particular the height profile portion, can be fixed to the actuating element, in particular it can be formed integrally with the actuating element. The reverse constellation is also possible: the at least one latching element can be attached to the actuating element and the at least one latching portion can be attached to the chamber door.

A latching element can comprise a mounting, which points upwards in a direction perpendicular to the pivoting plane, for a movably mounted sliding element, in particular, a ball. The sliding element can be spring-mounted in the mounting. The sliding element is adapted to engage in a latching recess of a latching portion, which is formed in particular in a height profile portion. The height profile portion is preferably integrated in a cavity or in a recess in the lower side of the actuating element. The height profile of the height profile portion is preferably provided to run along a circular ring path, which is concentric with the axis of rotation of the actuating element. A first latching recess can be provided to engage the actuating element in the first pivoted position and a second latching recess can be provided to engage the actuating element in the second pivoted position. In addition, the height profile is preferably configured in such a way that the mounting of the sliding element stops at predetermined elevated positions of the height profile, so that the actuating element, when properly mounted on the chamber door, can only be swiveled between the swivel positions corresponding to these elevated positions and not beyond them. The first and second swivel positions preferably correspond to the swivel positions corresponding to these raised positions. The correct closing of the closure device can be perceived by the user, in particular, by the latching of the position latching device.

Preferably the position latching device, in particular its height profile, is configured to be optionally mounted in such a way that an actuating element attached to the right edge of the chamber door can only be pivoted counterclockwise from the second pivot position to the first pivot position, or that an actuating element attached to the left edge of the chamber door can only be pivoted clockwise from the second pivot position to the first pivot position.

A further preferred feature is that the actuating element and in particular its position latching device, i.e. in particular the height profile and the complementary latching element plate, are configured in such a way that the actuating element and in particular its latching element plate can be mounted optionally on the left or right edge of a door. For this purpose, in particular, recesses and/or elevations distributed equidistantly along the height profile are provided. Due to this feature, the actuating element or the laboratory cabinet according to the invention can be efficiently and flexibly constructed or can be subsequently modified, since one and the same actuating element can be used in situations in which either a left-sided door hinge or a right-sided door hinge is required.

The laboratory cabinet device may comprise a housing, preferably an outer housing, whose housing walls are in contact with the environment. The chamber housing is then preferably located inside the outer housing. In this case, an incubator may have at least one chamber housing serving as an inner housing, which can be closed by at least one chamber door. In addition to the chamber door, an outer housing door may be provided which, in the closed position, adjoins the environment, wherein only the outer housing door adjoins the environment in the closed position and the chamber door, in the closed position of the outer housing door, is in a cavity situated between chamber housing, outer housing and outer housing door. The closure position is also known as the closing position.

In particular, the chamber door comprises a hinge device, which connects the chamber door pivotably to the chamber housing. Such a swivel door is moved by rotation between an open position and a closing position. The hinge device may in particular be located at the—in the intended use of the laboratory cabinet device—vertically oriented outer edge of a cuboid chamber housing adjacent to the chamber opening. The bottom plate of a cuboid chamber housing is arranged horizontally when the laboratory cabinet device is used as intended, the side walls of the chamber housing are arranged in particular vertically, and the top plate of the chamber housing is arranged, in particular, horizontally opposite the bottom plate. The closure device is preferably located at an outer edge of the chamber housing where the hinge device is not located, preferably in the closing position opposite the hinge device. However, a closure device can also be arranged alternatively or additionally at another outer edge of the chamber housing, in particular at a horizontally running outer edge.

The chamber door can also be a sliding door, which is moved by a translatory motion between an open position and the closing position. A mixed swivel/translatory motion of the chamber door is also possible.

The laboratory cabinet device may comprise more than one closure device, each of which, as defined, comprises holding elements which interact magnetically with each other in the closed position of the chamber door. In the case of several closure devices, these are preferably spaced apart in the closing position. In particular, they may be located on the same outer edge of the chamber housing or on different outer edges of the chamber housing. By providing several closure devices, the uniform closing of the housing door and the distribution of the closing forces acting between housing door and chamber housing can be optimized.

Preferably, the multiple closure devices are designed in an identical manner, comprising at least a first and a second holding element. However, it may also be provided that the multiple closure devices are configured in a different way, consisting of at least a first and a second holding element. In this way, the closure characteristics of the housing door, i.e. the force between the chamber housing and chamber door caused by the closure devices, applied against the deflection distance of the chamber door away from the closed position, can be influenced in the desired manner.

In the closed position, the outer housing door closes the inside of the housing preferably gas-tight, which is achieved in particular by at least one sealing device of the housing door or of the frame of the housing opening. In the closed position, the chamber door closes the inside of the chamber preferably gas-tight, which is achieved in particular by at least one sealing device of the chamber door or the frame of the chamber opening. However, the invention also concerns laboratory cabinet devices with a housing and/or a chamber housing, which does not completely seal the interior from the environment.

The closure device preferably has a group of magnetically acting holding elements which includes the first holding element which is arranged on the chamber housing, in particular is fixed there as a separate component or is integrated there, and a second holding element, which is arranged on the chamber door, in particular, which is fixed there as a separate component or is integrated there. The group of magnetically acting holding elements preferably comprises exactly two holding elements.

The magnetic effect of the holding elements is based on the fact that at least one holding element is configured as a magnetic element by having at least one magnet or consisting of at least one magnet. This is a permanent magnet in a particularly preferred embodiment. But it can also be an electromagnet.

Preferably, the group of magnetically acting holding elements comprises a magnetic element and in particular a magnetic element complementary to it for the formation of the magnetic attraction force, in particular by means of ferromagnetism. A holding device may comprise several magnetic elements which generate the desired magnetic force, in particular 2, 3, 4, 5, 6 magnetic elements or any other number. With such a configuration, the closure characteristics can be precisely adjusted and released again with precisely defined holding forces.

A holding element or magnetic element is preferably a separate component that is attached to the chamber housing and/or the chamber door when the laboratory cabinet device is installed. However, a holding element or magnetic element can also be an integral part of the chamber housing and/or the chamber door.

A magnetic element is preferably a permanent magnet or comprises a permanent magnet. Preferably the magnet comprises a cover element to protect it from mechanical damage or from corrosion.

Preferably the permanent magnet is made of a samarium-cobalt alloy or comprises these materials. These materials are extremely temperature resistant and have proven to be resistant to corrosion in humid or chemical laboratory environments and chamber interiors that must be heated to temperatures of up to 180° C., especially for sterilization purposes. However, it is also possible to use other permanent magnets.

Preferably, the laboratory cabinet device comprises at least one elastic element which, in the closed position, is arranged between the chamber housing and chamber door and, in particular, in the closed position between the chamber housing and chamber door, is compressed by the holding force of the closing device. The elastic element serves especially as a stop for the chamber door on the chamber housing, which mechanically cushions the contact of a chamber door on the chamber housing. In addition, the elastic element serves as an abutment for the holding force of the closing device, which compresses the elastic element in the closing position.

The elastic element is in particular a seal which, in the closed position, separates the inside of the chamber or the inside of the housing from the environment in a sealing manner. The seal is located in particular on an outer wall of the housing, which also comprises the housing opening, or is located on the outer wall of the chamber housing, which also comprises the chamber opening, i.e. in particular comprises the front side. The seal preferably runs continuously around the housing opening or chamber opening. Alternatively or in addition, such a seal can be arranged on the inside of the housing door or chamber door in such a way that in the closed position it runs continuously around the housing opening or chamber opening. The seal is preferably made of silicone or fluororubber or preferably consists of silicone or fluororubber. The silicone or fluororubber (FKM) may be foamed (silicone foam or fluororubber foam) and/or comprise one or more cavities and/or recesses. The desired elasticity or thermal insulation capacity of the seal is achieved through such pores or cavities. The sealing position is particularly characterized in that the chamber interior is closed by the chamber door, in particular hermetically sealed, and is hermetically sealed in particular by means of a seal. In the closed position, the elastically deformable element or seal is elastically deformed by the magnetic holding force of the closure device.

Preferably at least one holding element of a group of holding elements comprises a permanent magnet and at least one further holding element of this group comprises a material magnetically interacting with this permanent magnet.

Preferably the first holding element comprises a permanent magnet and the second holding element comprises a material magnetically interacting with this permanent magnet.

Preferably, the second holding element comprises a permanent magnet and the first holding element comprises a material magnetically interacting with this permanent magnet. This particular material can be configured as a portion of the chamber door or chamber housing.

Preferably, at least one holding element of a group of holding elements comprises a first permanent magnet and at least one further holding element of this group comprises a second permanent magnet magnetically interacting with this first permanent magnet. Preferably the first holding element has a first permanent magnet and the second holding element has a second permanent magnet magnetically interacting with this first permanent magnet. The first and second permanent magnets are preferably arranged with the same polarity in the closing position, so that there is an attracting effect between the first and second permanent magnet.

Preferably the at least one permanent magnet is a component of a holding element of the group of holding elements and in particular a component of a magnetic element. This preferably comprises a cover element or a socket, of which at least one permanent magnet is partially or completely enclosed.

Further preferred embodiments of the laboratory cabinet device according to the invention can be found in the description of the embodiments according to the figures.

It shows:

FIG. 4c schematically shows a view of the latching element plate, which is used with the position latching device in FIG. 4a.

FIG. 4d shows the actuating element of FIG. 4a as well as its height profile and the latching elements permanently mounted on the door in the first swivel position and when mounted on a right edge of the door as this is the case in FIG. 4a.

Figure 1:
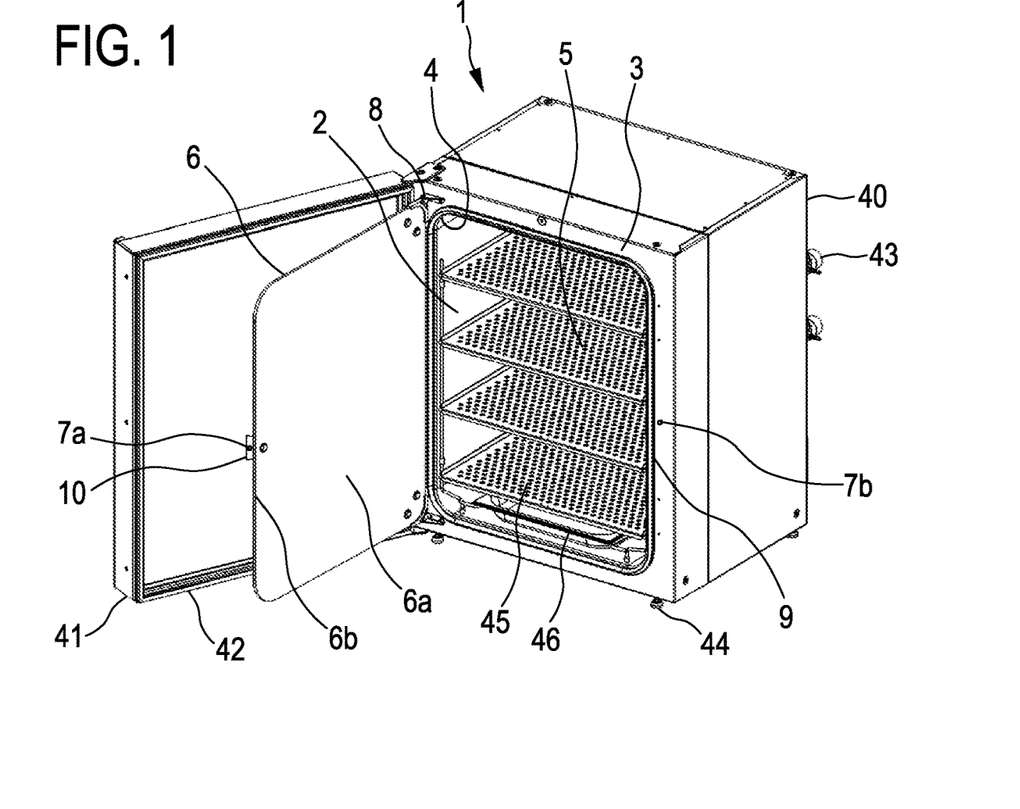
FIG. 1 shows a perspective view of an embodiment of a laboratory cabinet device according to the invention.

FIG. 1a shows a laboratory cabinet device 1 configured as a temperature control cabinet or heating cabinet for storing laboratory samples, more precisely a CO2 incubator for storing living cell cultures in a defined atmosphere at a controlled temperature, e.g. 37° C. For this purpose, the chamber interior 5 of the incubator is thermally insulated and can be sealed gas-tight against the environment. The gas composition in the interior is also regulated and can be changed via gas connections 43. The chamber housing 2 of the incubator stands on pedestals 44, encapsulates the interior 5 and opens into the front 3 of the incubator. The front side comprises the chamber opening 4, through which the chamber interior 5 is accessible. A transparent chamber door 6 serves to close the chamber opening in a closed position of the chamber door. In the incubator 1 the chamber housing 2 is placed inside the interior of an outer housing 40, so that the chamber housing 2 and the outer housing 40 are spaced apart and thermally insulated from each other. Inside the chamber shelf plates 45 and a humidifier tray 46 appear. The front side 3 of the chamber housing and the front side of the outer housing coincide in the present case.

Figure 2:
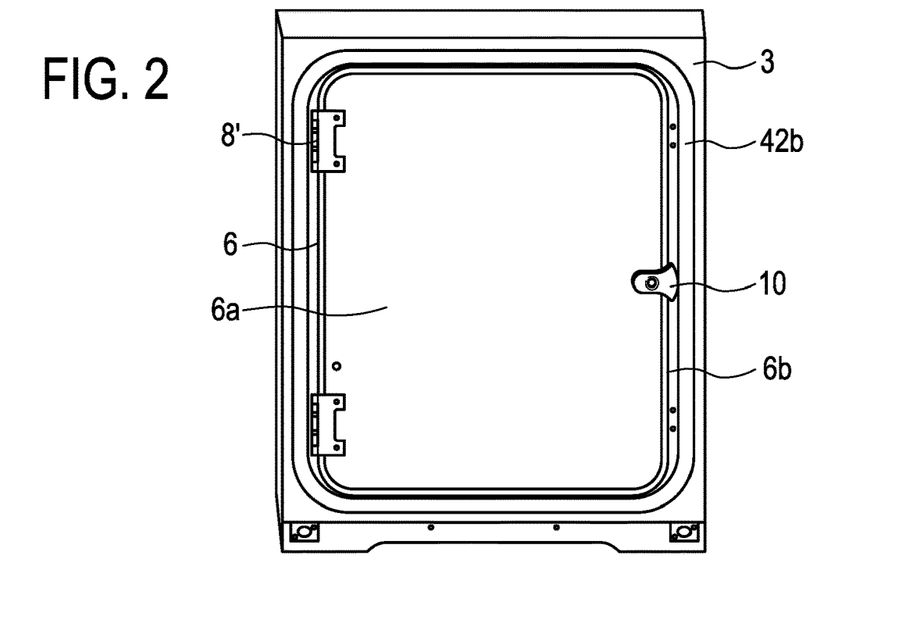
FIG. 2 shows a front view of an embodiment of a laboratory cabinet device according to the invention.

The outer door 41 and the chamber door 6 are shown in an open position. The outer door 41 is pivoted by hinges on the outer edge of the outer housing and has a circumferential silicone seal 42, which rests against the front in the closed position of the outer door and of the chamber door and thus frames the chamber door. The seal 42 can alternatively or additionally also be fitted as a seal 42b on the front side 3, see FIG. 2. As shown in FIG. 2, an additional circumferential seal 42b can be provided on the front side 3, against which the seal 42 rests in the closed position. The chamber opening 4 is framed by a silicone seal 9, which is fitted on the front side 3, which alternatively or in addition, can also be fitted as seal 9' on the inside of the chamber door 6.

When the outer door 41 has been opened, the chamber door 6 of the incubator is initially still closed. The closure device (10, 7a, 7b) serves this purpose. With the chamber door 6 closed, the user can first view the interior 5 through the transparent door wall before opening the door and inserting or removing a laboratory sample.

In order to protect the stored laboratory samples, it is important in the case of laboratory cabinet devices or temperature control cabinets to minimize the time during which the interior of the cabinet is exposed to the environment. The present invention is based on the observation that the opening time intervals can be influenced by the configuration of the closing mechanism by which the chamber door is held and closed in the closing position. Therefore, a laboratory cabinet device was developed with a closure device that can be efficiently actuated by the user to minimize the opening time.

Figure 3A:
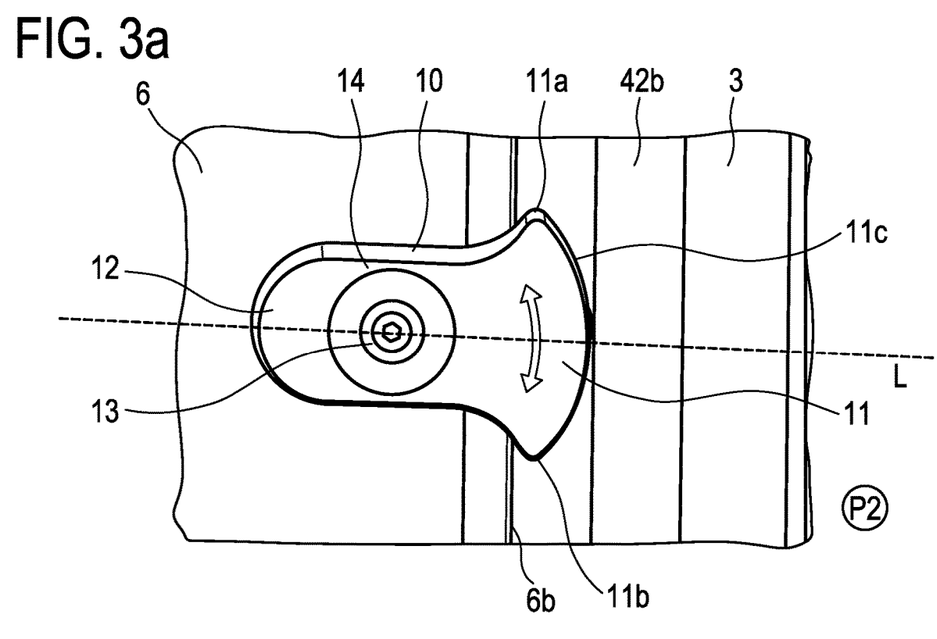
FIG. 3a shows a closure device, which is used in a laboratory cabinet device according to the invention in FIG. 1 or 2, in a perspective front view in the second pivot position of the actuating element, closed pivot position (P2), closed position of the chamber door.
Figure 3B:
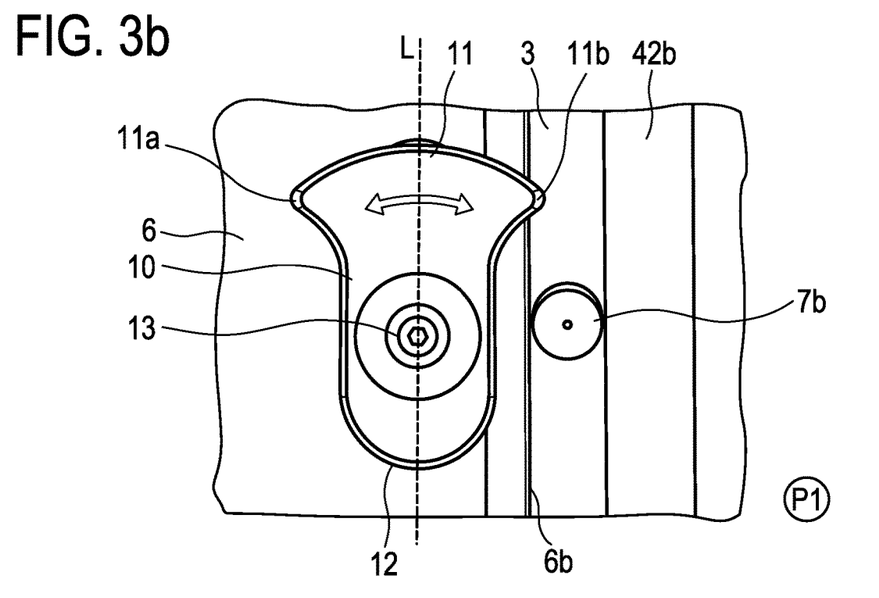
FIG. 3b shows the closure device of FIG. 3a, in a perspective front view in the first pivot position of the actuating element and in the open position of the chamber door.

The closure device serves to hold the chamber door 6 on the front side 3 in the closing position by a magnetic holding force and comprises an actuating element 10, a first holding element 7a and a second holding element 7b. The first holding element 7a is attached to the actuating element 10 and the second holding element 7b is attached to the front side 3. The actuating element 10 is pivotally mounted on the chamber door 6 so that the actuating element 10 is pivotally movable between a first, open position P1 (shown in FIG. 3b), in which the first and second holding elements do not exert a magnetic holding force on each other, and a second, closed position P2 (shown in FIG. 3a), in which the first and second holding elements exert the magnetic holding force on each other. The actuating element 10 is arranged in parallel to the main plane 6a of the chamber door 6 and comprises a first end 11. This end of the actuating element 10 is advantageously configured as a grip tab portion 11, which in the second position projects beyond the edge 6b of the chamber door 6, so that in the second position P2 the magnetic holding force of the closure device can be overcome by the user both by rotating the actuating element 10 from the second position P2 to the first position P1 and by pulling the chamber door by means of the grip tab portion in a direction (A) perpendicular to the main plane 6a of the chamber door 6.

Configuring the actuating element with a grip tab portion and due to the possibility of overcoming the magnetic holding force both by swiveling the actuating element and by pulling on the actuating element a compact and efficiently actuated closure device is realized. The use of the magnetically interacting holding elements 7a, 7b eliminates the requirement of conventional bolt closures acting by mechanical form closure, i.e. having to swivel the actuating element first before opening the chamber door or having to hold the actuating element in a swiveled position before closing the chamber door. The grip tab portion allows intuitive operation of the actuating element. Almost every movement of the grip tab portion intuitively performed by the user leads to the desired opening or closing of the magnetic closure. During the incubator's operating time, this reduces the time required for different users to learn and complete actuating the chamber door closure. In particular, one-handed operation of the closing device is facilitated, since the operation is independent of the subjective preferences of the user, the operation with the right or left hand or even with another part of the body or of an aid, and independent of whether the closure device is mounted on the left side or the right side of the chamber door. The operating element 10 is a plate-shaped component. It has a recess or a cavity 16, which is advantageously used here to accommodate further functional components.

Figure 5:
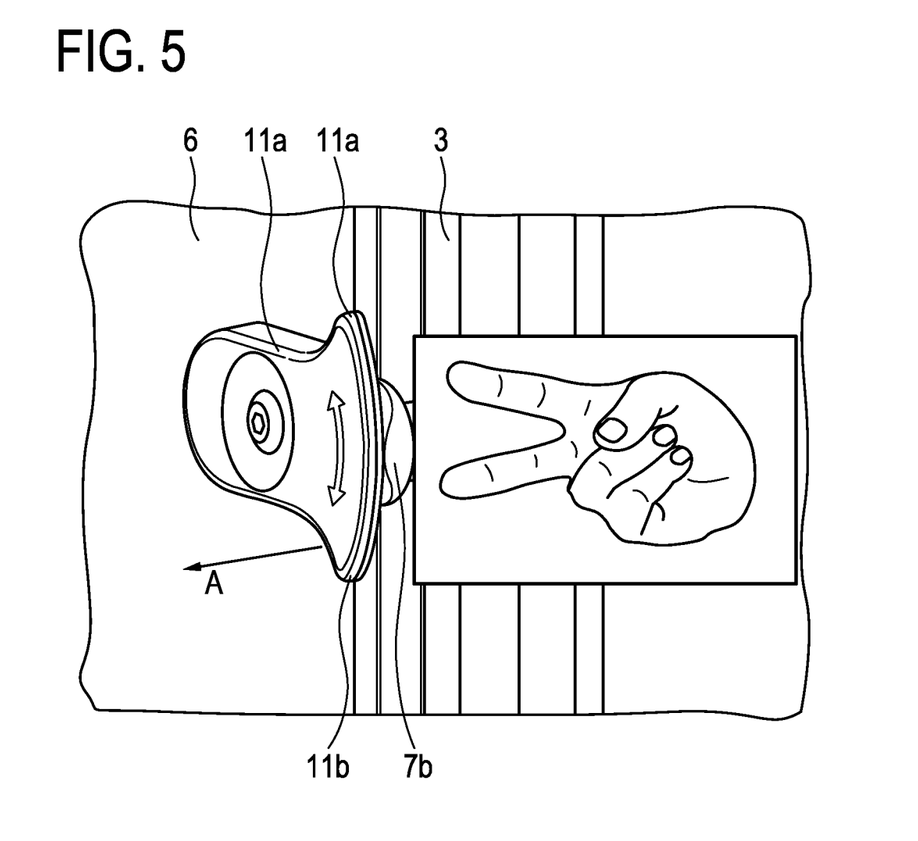
FIG. 5 shows the closure device of FIG. 3a, in a perspective side view and in the second swivel position of the actuating element and in a closed position of the chamber door.

The actuating element 10 has an elongated plate body 14, which comprises the grip tab portion 11 as the first end and an end section 12, in the present case rounded off in a circle, as the second end. A hole 15 perpendicular to the plate plane of the actuating element serves to accommodate a rotary axis element 13, by means of which the actuating element 11 is pivotally mounted on the chamber door 6. The grip tab portion 11 has the first retaining element 7a on its lower side facing the front side 3 in its closed position (not visible in FIG. 3a, 3b). The grip tab portion 11 has a first wing portion 11a and a second wing portion 11b, which are integrally formed with the grip tab portion 11 and the actuating element 10 respectively. The wing portions 11a and 11b protrude laterally from the plate body 14 parallel to the plane of the plate body 14 and the main plane 6a of the chamber door respectively, so that a finger of the user in position P2 can engage behind the respective first and/or second wing portion to open the chamber door by pulling. The grip tab portion and the wing portions protrude laterally, especially with respect to the first holding element 7a parallel to the plane of the panel body 14 or to the main plane 6a of the chamber door, so that it is easier to reach behind the grip tab section. This is shown in FIG. 5.

The first holding element 7a is in present case configured as a plate element made of magnetic stainless steel, which is inserted into a recess on the lower side of the grip tab portion and screwed and/or glued into place. The holding element 7a can also be spring-mounted on the actuating element 10, in order to allow an evasive movement of the retaining element in direction A perpendicular to the plane of the plate body 14 or the main plane 6a of the chamber door. Alternatively, the first holding element could also be configured as a permanent magnet or comprises at least one such magnet. The pole direction of the permanent magnet may in this case correspond to the pole direction of the permanent magnet of the second holding element, if the second holding element is also designed as a permanent magnet or comprises one, in order to generate the desired attractive magnetic force in closing position P2.

The second holding element is here configured as a permanent magnet, which is enclosed and thus protected in a socket, which is attached to the front side 3. The permanent magnet is selected such that it tolerates the operating temperature of the temperature control cabinet. In the case of the incubator, whose interior is sterilized especially at heating temperatures above 110° C., a samarium-cobalt alloy was therefore chosen as the material. The second holding element can also be configured as a ferromagnetic partner of a first holding element comprising the permanent magnet.

In the closure position of the chamber door and in position P2 of the actuating element, the first and second holding elements are situated against each other and adhere to each other due to the magnetic attraction force. By turning the actuating element from position P2 to position P1, this attraction force can be overcome much more easily and comfortably than by pulling into direction A. In the open position of the chamber door 6, when the actuating element 10 is arranged in the position P2, the closing of the chamber door automatically leads to the closing of the magnetic closure by the magnetic holding force moving the first and second holding elements directly towards each other within the influence of the magnetic force. The attachment of the holding elements can also be perceived as a "click", so that the user receives an acoustic feedback about the successful closing of the chamber door.

The closure device in the present case also comprises a position latching device 21, 25 by means of which the actuating element engages in the second position and latches in a first position. In the second position the actuating element is arranged horizontally, i.e. its longitudinal axis L, see FIG. 3a, extends horizontally. In the first position the actuating element is arranged vertically, i.e. its longitudinal axis L, see FIG. 3b, extends vertically. In a top view along the axis A, the actuating element is formed mirror-symmetrical to the longitudinal axis L. The position latching device comprises a latching element plate 20, on which at least one latching element 21 is arranged. In the present case three latching elements 21, 21', 21" are provided equidistantly arranged on the latching element plate 20 along a circular path B, wherein the circular path is concentric with the bearing axis 23 of the latching element plate 20 and coincides with the circular path of the height profile. When the actuating element is mounted on the chamber door as intended, the latching element plate 20 is fixed to the chamber door by the pivot axis element, while the actuating element 10 is arranged rotatably about the sliding sleeve, which is arranged concentrically with the pivot axis A. The pivot axis element 13 comprises a head portion at the end, which is located in the direction of axis A. A nut 19 is provided to clamp the latching plate 20 against the chamber door while the actuating element remains rotatable.

Figure 4A:
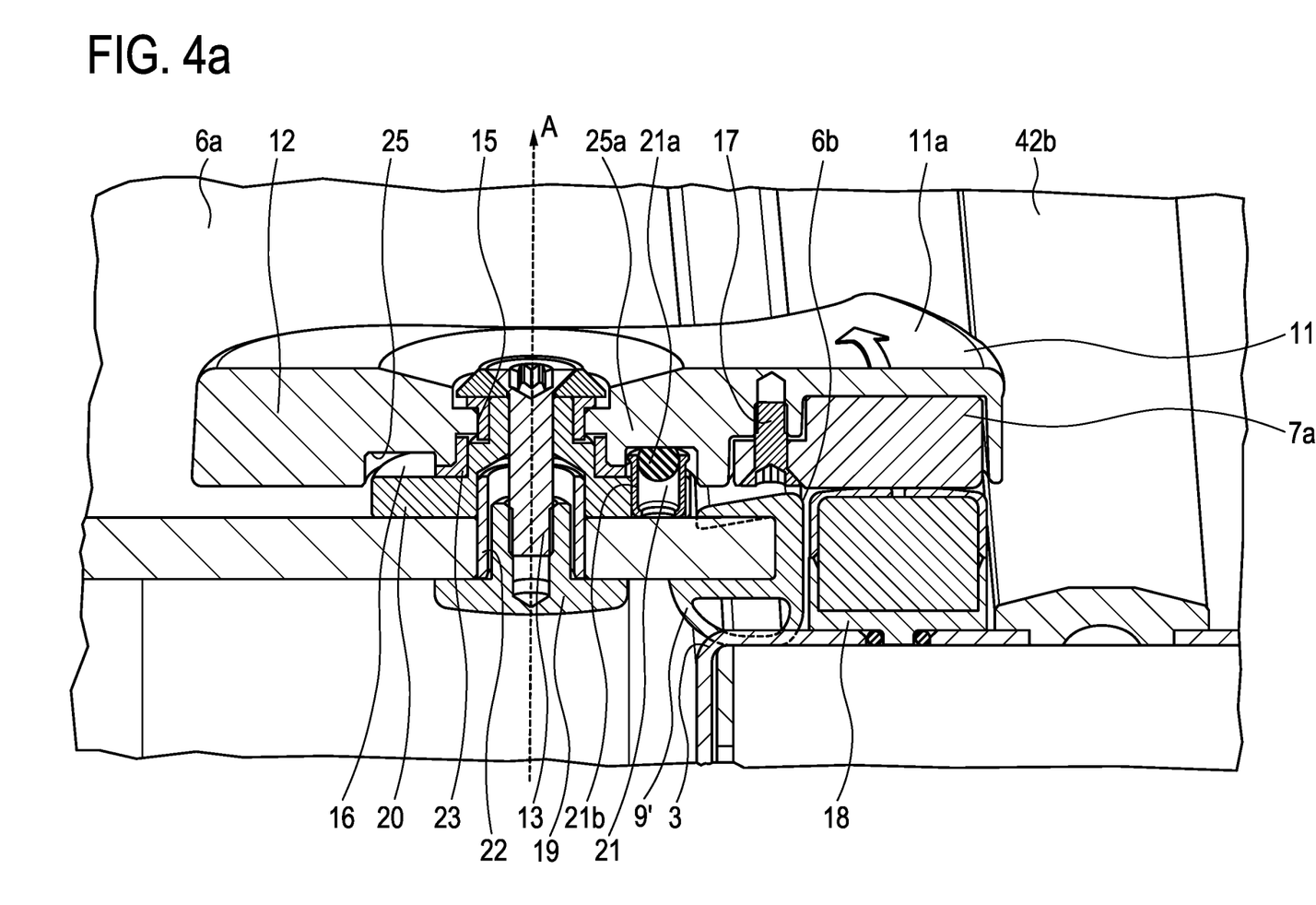
FIG. 4a shows a perspective cross-sectional view through the closure device of FIG. 3b, wherein the cross-section extends perpendicular to the pivoting plane of the actuator and along its longitudinal axis (L).
Figure 4B:
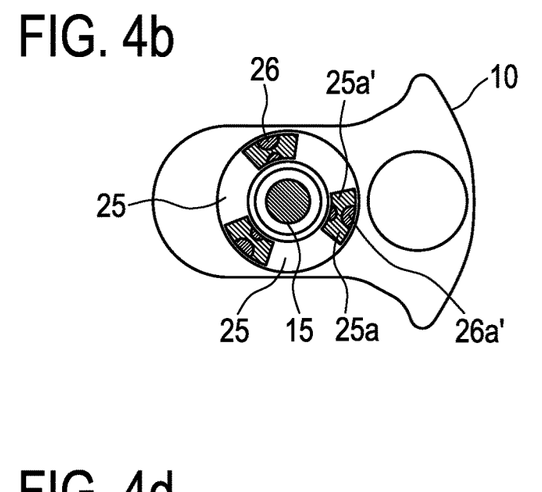
FIG. 4b schematically shows a view of the height profile of a position latching device, formed on the lower side, which faces towards the chamber door of the actuating element in FIG. 3b.
Figure 4C:
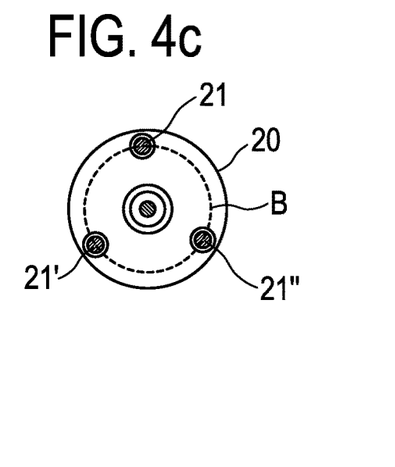

The latching element 21 comprises a ball mount 21b, which points upwards in the direction of axis A with a spring-loaded ball 21a. The ball is adapted to engage into latching recesses 25a, which are formed in a height profile 25. The height profile 25 is presently integrated in the cavity 16 or in the lower side of the actuating element 10. The height profile is provided along a circular railway 25, which is concentric with hole 15 of the actuating element. A first latching recess 25a' may be provided to engage the actuating element in the first pivoted position, the second latching recess 25a' may be provided to engage the actuating element in the second pivoted position. The height profile is also configured so that the ball mount of the latching element stops at elevated positions 26a', 26a of the height profile, so that the actuating element, when properly mounted on the chamber door, can only be pivoted between the first and second pivot positions and not beyond. The first and second pivot positions correspond to the first and second latching positions respectively. In order to achieve the desired strength of the latching connection in the first and second pivot position, the height profile 25 along the circular path has three equally spaced pairs 25a', 25a of latching recesses, each separated by a raised structure 26a'. In principle, however, only at least one pair 25a', 25a of latching recesses must be provided in order to achieve engagement in the first and second pivot position.

A particular feature of the actuating element at present, is that the position latching device 21, 25, in particular the height profile 25, is configured to be mounted optionally in such a way that an actuating element fastened to the right edge of the chamber door can be pivoted from the second pivot position only counter-clockwise as far as the first pivot position, or that an actuating element fastened to the left edge of the chamber door can be pivoted from the second pivot position only clockwise as far as the first pivot position. This is achieved by the raised positions 26a', 26a in the height profile 25, which cannot be passed by the latching element, which is permanently mounted on the door. In principle, a different opening logic would also be possible: it is also possible to mount the actuating element in such a way that, when mounted on the right-hand side, it is swiveled from the horizontal (position closed) clockwise downwards to the vertical (position open) by 90° degrees. For left-hand installation, it is also possible to mount the actuating element in such a way that it can be swiveled from the horizontal (position closed) counterclockwise downwards to the vertical (position open) by 90° degrees.

Figure 4D:
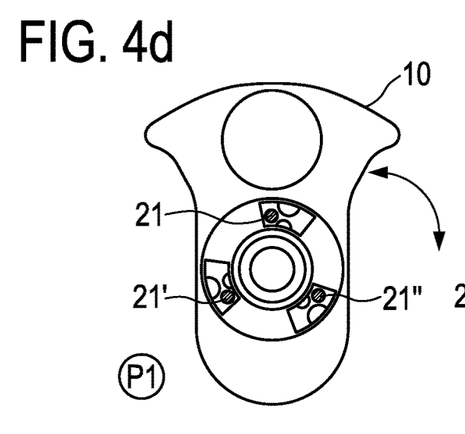
Figure 4E:
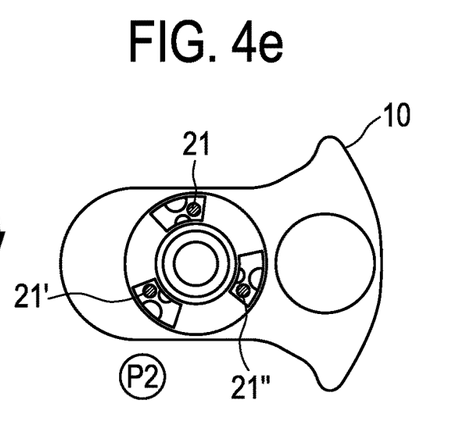
FIG. 4e shows the actuating element of FIG. 4a as well as its height profile and the latching elements permanently mounted on the door in the second swivel position and when mounted on a right edge of the door.
Figure 4F:
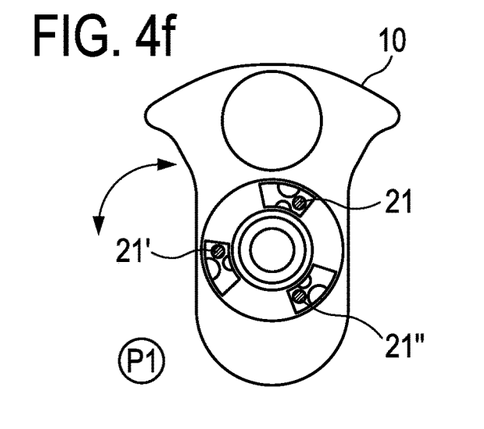
FIG. 4f shows the actuating element of FIG. 4a as well as its height profile and the latching elements attached to the door slightly twisted in relation to FIGS. 4d and 4e in the first swivel position when mounted on a left edge of the door.
Figure 4G:
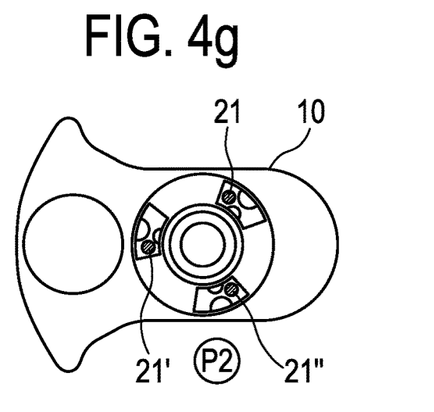
FIG. 4g shows the actuating element of FIG. 4a as well as its height profile and the latching elements mounted on the door slightly rotated in relation to FIGS. 4d and 4e in the second swivel position when mounted on a left edge of the door.

Another particular feature is that the actuating element 10 and in particular its height profile and the complementary latching element plate with latching elements are configured in such a way that the actuating element and its latching element plate can be mounted either on the left or on the right edge of a door. This property results from the structure and relative arrangement of latching element plate and height profile. In FIG. 4d an actuating element 10 mounted on the right edge of a door is shown in the first pivot position P1, in FIG. 4e it is shown in the second pivot position P2. The position of the latching element plate or of the latching elements 21, 21', 21", which are fixed to the door not shown, are identical in FIGS. 4d and 4e. In FIG. 4f the same actuating element 10 is now mounted on the left edge of a door and shown in the first pivot position P1, whereas in FIG. 4e it is shown in the second pivot position P2. The position of the latching element plate or of the latching elements 21, 21', 21", which are fixed to the door not shown, are identical in FIGS. 4f and 4g. The only difference when mounted on the right or left edge of a door is that in both cases, although the same latching element plate (or the same latching elements) is used, when mounted on the left side of the door it is placed in a slightly rotated position compared to the right side mounting. This results directly from FIGS. 4d to 4g. Due to this property, the actuating element 10 or the laboratory cabinet device according to the invention can be efficiently and flexibly constructed, as one and the same actuating element 10 can be used in situations, where either a left-sided door hinge or a right-sided door hinge is required.

The invention claimed is:

1. Laboratory cabinet device (1) for storing laboratory samples, comprising a chamber housing (2) with a front side (3) and a chamber opening (4) of the front side through which the chamber interior (5) is accessible, a chamber door (6) for closing the chamber opening in a closed position of the chamber door,
   closure device (10, 7a, 7b) for holding the chamber door at the front side in the closed position by a magnetic holding force, wherein the closure device comprises an actuating element (10), a first holding element (7a) and a second holding element (7b),
   wherein the first holding element (7a) is fixed to the actuating element (10) and the second holding element (7b) is fixed to the front side (3), and the actuating element (10) is pivotally mounted to the chamber door (6) so that the actuating element (10) is pivotally movable between a first open pivoted position (P1), in which the first and second holding elements cannot exert magnetic holding force on each other, and a second, closed pivoted position (P2), in which the first and second holding elements can exert the magnetic holding force on each other,
   wherein the actuating element (10) extends parallel to the main plane (6a) of the chamber door (6) and has an end which is formed as a grip tab portion (11) which in the second pivoted position projects beyond the edge (6b) of the chamber door (6) so that in the closed position of the chamber door and in the second pivoted position (P2) of the actuating element (10) the magnetic holding force of the closure device (10, 7a, 7b) can be overcome by the user both by rotating the actuating element (10) from the second pivot position (P2) to the first pivot position (P1) and by pulling the chamber door by means of the grip tab portion (11) in a direction (A) perpendicular to the main plane (6a) of the chamber door (6).

2. A laboratory cabinet device according to claim 1, wherein the first and/or the second holding element comprise or consist of a permanent magnet.

3. A laboratory cabinet device according to claim 1, wherein the actuating element is a plate-shaped component (10), whose main plane runs parallel to a pivoting plane and to the main plane (6b) of the chamber door (6).

4. Laboratory cabinet device according to claim 1, wherein the actuating element comprises a hole or recess through which a pivot member oriented parallel to the pivot axis of the actuating element is disposed and pivotally connects the actuating element to the chamber door.

5. Laboratory cabinet device according to claim 1, wherein the first holding element is arranged on the lower side of the grip tab section (11), which faces towards the chamber door in the first pivoted position (P1).

6. Laboratory cabinet device according to claim 1, wherein the grip tab portion comprises at least one tab portion which, in the second pivoted position (P2), projects beyond the edge (6b) of the chamber door in a pivoting plane of the actuating element.

7. Laboratory cabinet device according to claim 6, wherein the at least one tap portion includes a first wing portion (11a) and a second wing portion (11b) protruding laterally from the actuating element perpendicular to the longitudinal direction (L) of the actuating element, which corresponds to the radial direction of the pivoting movement.

8. Laboratory cabinet device according to claim 1, wherein the closure device comprises a position latching device (21, 25) by means of which the actuating element engages at least in the second pivoted position and/or at least also engages in a first pivoted position.

9. Laboratory cabinet device according to claim 8, wherein the position latching device comprises at least one latching element (21a) and at least one latching portion (25a), which latch together at least in the first and/or in the second pivoted position.

10. Laboratory cabinet device according to claim 1, which is a tempering cabinet for tempering laboratory samples.

11. Laboratory cabinet device according to claim 10, which is an incubator for cell culture.

\* \* \* \* \*